US 7,687,471 B2

(12) United States Patent
Hayes et al.

(10) Patent No.: US 7,687,471 B2
(45) Date of Patent: Mar. 30, 2010

(54) BENZIMIDAZOLE NON-AQUEOUS COMPOSITIONS

(75) Inventors: Jon C. Hayes, East Brunswick, NJ (US); Debora L. Guido, Bordentown, NJ (US); Jacob A. Zupan, Yardley, PA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/634,027

(22) Filed: Dec. 5, 2006

(65) Prior Publication Data

US 2007/0128239 A1 Jun. 7, 2007

Related U.S. Application Data

(60) Provisional application No. 60/742,724, filed on Dec. 6, 2005.

(51) Int. Cl.
*A01N 43/04* (2006.01)
*A01N 43/52* (2006.01)
*A61K 31/70* (2006.01)

(52) U.S. Cl. .......................................... 514/30; 514/395

(58) Field of Classification Search ....................... None
See application file for complete search history.

(56) References Cited

U.S. PATENT DOCUMENTS 5,840,324 A 11/1998 Hennessy et al.
6,267,985 B1 * 7/2001 Chen et al. .................. 424/451
2005/0245468 A1 11/2005 Rowe et al.
2006/0121072 A1 6/2006 Shepherd

FOREIGN PATENT DOCUMENTS

| FR | 2755824 A1 * | 5/1998 |
| WO | WO 00/74489 A1 | 12/2000 |
| WO | WO 01/05232 A1 | 1/2001 |
| WO | WO 03/092680 A1 | 11/2003 |
| WO | WO 2004043445 A1 * | 5/2004 |

OTHER PUBLICATIONS

CN 02153428, Nov. 11, 2002, machine translation of claims.*
Derrieu et al. FR 2755824, May 22, 1998, English translation.*

* cited by examiner

*Primary Examiner*—Shaojia Anna Jiang
*Assistant Examiner*—Layla Bland
(74) *Attorney, Agent, or Firm*—Gloria K. Szakiel; Barbara L. Renda

(57) ABSTRACT

The present invention provides a stable veterinary oral composition which comprises one or more surfactants, a water-miscible solvent, optionally an oil and an effective amount of each of a benzimidazole antihelmintic compound, such as triclabendazole and a macrocyclic lactone, such as moxidectin. Said composition is useful for treating and controlling endo- and ectoparasitic infection and infestation in a homeothermic animal.

18 Claims, No Drawings the benefit under 35 U.S.C. §119
BENZIMIDAZOLE NON-AQUEOUS COMPOSITIONS

BACKGROUND OF THE INVENTION

This application claims the benefit under 35 U.S.C. §119 (e) to U.S. provisional application No. 60/742,724, filed Dec. 6, 2005, which is hereby incorporated by reference in its entirety.

The benzimidazoles are the largest chemical family used to treat endoparasitic diseases in domestic animals. They are characterized by a broad spectrum of activity and a wide safety margin. Their high degree of efficacy and low toxicity are often sought after in agronomic practice. However, they are sparingly soluble in water and are generally administered orally as a suspension or paste or by intraruminal injection. Although oral administration of benzimidazoles in ruminants and horses is particularly effective, a suspension or paste formulation generally causes manufacturing, storage and stability problems. Further, it is often desirable to combine the benzimidazole with a macrocyclic lactone to broaden the spectrum of parasites controlled to include ectoparasites and those endoparasites which may be missed by the benzimidazole. However, the physical and chemical stability of the macrocyclic lactone may be compromised in a routine suspension or paste formulation.

Therefore, it is an object of this invention to provide an effective oral veterinary composition containing a benzimidazole and a macrocyclic lactone, which is a stable homogeneous clear solution.

It is another object of the invention to provide a method for the prevention, treatment and control of endo- and ectoparasitic infection or infestation in an animal, particularly a homeothermic animal.

Other objects and features of the invention will become more apparent from the detailed description set forth hereinbelow.

SUMMARY OF THE INVENTION

The present invention provides a stable, non-aqueous, oral, veterinary composition which comprises one or more surfactants, a water-miscible solvent, optionally an oil and an effective amount of each of a benzimidazole and a macrocyclic lactone.

Also provided are a method for the treatment and control of parasitic infection and infestation in a homeothermic animal and a process for the preparation of a non-aqueous oral veterinary parasiticidal composition.

DETAILED DESCRIPTION OF THE INVENTION

Benzimidazoles are used to treat endoparasitic diseases in domestic animals and are characterized by a broad spectrum of activity and low toxicity. Benzimidazoles of current interest include thiabendazole, cambendazole, parbendazole, mebendazole, fenbendazole, oxfendazole, oxibendazole, albendazole, albendazole sulfoxide, thiophanate, febantel, netobimin, and triclabendazole. It is often desirable to administer the benzimidazole compound in combination with a macrocyclic lactone such as milbemycin D; avermectin; ivermectin; abamectin; doramectin; moxidectin or the like to enhance the spectrum of parasites to be controlled. Benzimidazoles and macrocyclic lactones offer complimentary parasite control in homeothermic animals. For example, triclabendazole is active against liver flukes but not round worms or ectoparasites and moxidectin is active against round worms and ectoparasites, but is less active as a flukicide.

Ideally, veterinary compositions containing both a benzimidazole and a macrocyclic lactone would be stable, bioavailable and easy to administer. Because benzimidazoles have very limited solubility in water, they are often formulated as suspensions or pastes. However, suspension and paste compositions frequently exhibit caking and sedimentation which cause manufacturing, storage and stability problems. Further, in order to obtain sufficient bioavailability, micronization of the benzimidazole is generally required in the formulation process of a suspension or paste. Moreover, paste formulations may retain their structure and are often spit out of the animal's mouth.

Surprisingly, it has now been found that a benzimidazole and a macrocyclic lactone may be formulated as a clear, homogeneous, non-aqueous solution suitable for oral administration to a homeothermic animal. Advantageously, the composition of the invention is self-emulsifying so that the benzimidazole active ingredient does not precipitate in the stomach but remains bioavailable. Since the benzimidazole remains in solution, no micronization is required in the preparation of the inventive composition. The oral veterinary composition of the invention comprises one or more surfactants, a water-miscible solvent, optionally an oil and an effective amount of each of a benzimidazole and a macrocyclic lactone.

Surfactants suitable for use in the inventive composition include non-ionic surfactants such as sucrose monolaurate, sorbitan monooleate or polysorbate 80; polyethylene glycol 660 hydroxystearate; polyoxyl 35 castor oil; PEG-60 hydrogenated castor oil or the like, or a mixture thereof, preferably sorbitan fatty acid esters, more preferably sorbitan monooleate or polysorbate 80 or a mixture thereof.

Water-miscible solvents suitable for use in the inventive composition include pharmaceutically acceptable water-miscible solvents, for example alcohols such as benzyl alcohol, ethanol, or the like; glycols such as polyethylene glycol, propylene glycol, glycerin, or the like, preferably alcohols or glycols or a mixture thereof, more preferably benzyl alcohol, ethanol, polyethylene glycol, propylene glycol, or a mixture thereof.

Oils suitable for use in the inventive composition include pharmaceutically acceptable oils, for example propylene glycol dicaprylate/dicaprate, caprylic/capric triglyceride, or the like, preferably propylene glycol dicaprylate/dicaprate.

Benzimidazoles suitable for use in the inventive composition include thiabendazole, cambendazole, parbendazole, mebendazole, fenbendazole, oxfendazole, oxibendazole, albendazole, albendazole sulfoxide, thiophanate, febantel, netobimin, or triclabendazole, preferably triclabendazole.

Macrocyclic lactones suitable for use in the composition of the invention include milbemycin D, avermectin, ivermectin, abamectin, doramectin, or moxidectin, preferably moxidectin.

The effective amounts of the benzimidazole and macrocyclic lactone compounds may vary according to the potency of the compounds, the method of application, the host animal, the target parasite, the degree of infestation, or the like. In general, amounts of about 2-10% w/v, preferably 3-7% w/v, of a benzimidazole such as triclabendazole may be suitable and amounts of about 0.01-2.0% w/v, preferably 0.05-1.0% w/v, more preferably about 0.07-0.3% w/v of a macrocyclic lactone such as moxidectin may be suitable.

Surfactants may be present in the inventive composition in amounts of 1.0-75.0% w/v, preferably 2.5-60.0% w/v. The oil may be present in amounts of about 0-70% w/v, preferably about 10-70% w/v, more preferably about 25-65% w/v.

As used in the specification and claims, the term "benzimidazole" designates a veterinary compound in the benzimidazole chemical family such as thiabendazole, cambendazole, parbendazole, mebendazole, fenbendazole, oxfendazole, oxibendazole, albendazole, albendazole sulfoxide, thiophanate, febantel, netobimin, or triclabendazole. As used in the specification and claims, the term "macrocyclic lactone" designates a pharmaceutical compound in the avermectin or milbemycin family of compounds including avermectins such as ivermectin, abamectin or doramectin and milbemycins such as milbemycin D or moxidectin.

As used herein, the term "w/w" designates weight/weight, the term "w/v" designates weight/volume, and the term "mg/kg" designates milligrams per kilogram of body weight.

Advantageously, the stable, oral, parasiticidal, veterinary composition of the invention provides easy administration and effective bioavailability of active ingredients. Accordingly, the present invention provides a method for the treatment and control of endo- and ectoparasitic infection or infestation in an animal, particularly a homeothermic animal, which comprises orally administering to said animal a composition which comprises one or more surfactants, a water-miscible solvent, optionally an oil and an effective amount of each of a benzimidazole and a macrocyclic lactone.

Examples of oral administrations suitable for use in the method of the invention include gavage or drench or any of the conventional means of orally applying a liquid veterinary composition, preferably a drench.

Homeothermic animals suitable for treatment in the method of the invention include: swine, cattle, sheep, horses, goats, camels, water buffalos, donkeys, fallow deer, reindeer, or the like, preferably swine, cattle, horses or sheep.

In actual practice, the composition of the invention may be administered in dose rates of mg of active ingredient per kg of body weight of the host animal. Dose rates suitable for use in the method of invention will vary depending upon the mode of administration, the species and health of the host animal, the target parasite, the degree of infection or infestation, the breeding habitat, the potency of the additional parasiticidal compound, and the like.

The present invention also provides a process for the preparation of an oral veterinary parasiticidal composition which comprises: admixing one or more surfactants and optionally an oil to form a uniform mixture; dissolving a macrocyclic lactone in said mixture to form a solution; and mixing said solution with a benzimidazole and a water-miscible solvent.

Macrocyclic lactones suitable for use in the process of the invention include milbemycin D, avermectin, ivermectin, abamectin, doramectin, or moxidectin, preferably moxidectin.

Benzimidazoles suitable for use in the process of the invention include thiabendazole, cambendazole, parbendazole, mebendazole, fenbendazole, oxfendazole, oxibendazole, albendazole, albendazole sulfoxide, thiophanate, febantel, netobimin, or triclabendazole, preferably triclabendazole.

For a more clear understanding of the invention, the following examples are set forth hereinbelow. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLE 1

Preparation of an Endo- and Ectoparasiticidal Oral Composition

| Component Description | w/v % |
|---|---|
| moxidectin | 0.100 |
| triclabendazole | 5.00 |
| PEG-35 castor oil | 60.00 |
| propylene glycol dicaprylate/dicaprate | q.s.* |
| benzyl alcohol | 4.00 |

*quantity sufficient to obtain a total of 100% w/v

Method of Preparation

A portion of the propylene glycol dicaprylate/dicaprate is mixed with PEG-35 castor oil until uniform. The mixture is treated with benzyl alcohol, followed by moxidectin and stirred until solution is complete. The solution is treated slowly with triclabendazole and mixed until solution is complete. The remaining portion of the propylene glycol dicaprylate/dicaprate is added and mixing is continued until a clear homogeneous solution is obtained.

EXAMPLES 2-4

Preparation of Endo- and Ectoparasiticidal Oral Compositions

Using essentially the same procedure described in Example 1 hereinabove, the compositions shown below are prepared.

| Component Description | Ex. 2 w/v % | Ex. 3 w/w % | Ex. 4 w/w % |
|---|---|---|---|
| moxidectin | 0.100 | 0.100 | 0.100 |
| triclabendazole | 5.00 | 5.00 | 5.00 |
| sorbitan monooleate | 5.00 | 5.00 | 2.5 |
| PEG-35 castor oil | 40.00 | — | — |
| polysorbate 80 | — | 40.00 | 30.00 |
| propylene glycol dicaprylate/dicaprate | q.s.* | q.s.* | q.s.* |
| benzyl alcohol | 4.00 | 4.00 | 4.00 |

*quantity sufficient to obtain a total of 100% w/v

EXAMPLE 5

Preparation of Endo- and Ectoparasiticidal Compositions

| Component Description | w/v % |
|---|---|
| moxidectin | 0.100 |
| triclabendazole | 5.00 |
| sucrose monolaurate | 10.00 |
| ethanol | 20.00 |
| PEG 400 | q.s.* |

*quantity sufficient to obtain a total of 100% w/v

Method of Preparation

Sucrose monolaurate is slowly added to ethanol and mixed until solution is complete. Moxidectin is added and the mixture is stirred until solution is complete. A portion of PEG 400 is added and the mixture is stirred until solution is homogeneous, then triclabendazole, is slowly added and stirring is continued until solution is complete. The remaining portion of PEG 400 is added and the resultant mixture is stirred until a clear homogeneous solution is obtained.

EXAMPLE 6

Evaluation of the Plasma Levels of Test Compositions

In this evaluation, test compositions prepared in Examples 1-5 and a conventional moxidectin/triclabendazole-containing suspension were orally administered to sheep. Blood samples were drawn over the course of 29 hours after treatment and assayed for triclabendazole metabolites and moxidectin. The blood levels for the assayed components for test compositions 1-5 were approximately equal to or greater than the levels for the conventional suspension composition.

What is claimed is:

1. An oral veterinary composition which comprises:
   a benzimidazole compound;
   moxidectin;
   one or more surfactants in an amount between 30% w/v and 60% w/v;
   a pharmaceutically acceptable oil in an amount of about 25-65% w/v; and
   a water miscible solvent,
   wherein the composition is non-aqueous.

2. The composition according to claim 1 wherein said benzimidazole is selected from the group consisting of: thiabendazole; cambendazole; parbendazole; mebendazole; fenbendazole; oxfendazole; oxibendazole; albendazole; albendazole sulfoxide; thiophanate; febantel; netobimin; and triclabendazole.

3. The composition according to claim 1 wherein the water-miscible solvent is selected from the group consisting of: an alkylene glycol; a polyalkylene glycol; an alcohol; and a mixture thereof.

4. The composition according to claim 1 wherein the composition comprises about 2-10% w/v of a benzimidazole and about 0.01-2.0% w/v of a macrocyclic lactone.

5. The composition according to claim 2 wherein said benzimidazole is triclabendazole.

6. The composition according to claim 1 wherein the oil is propylene glycol dicaprylate/dicaprate.

7. The composition according to claim 1 wherein the oil is caprylic/capric triglyceride.

8. A process for the preparation of a composition according to claim 1 which comprises: admixing one or more surfactants and an oil to form a uniform mixture; dissolving moxidectin in said mixture to form a solution; and mixing said solution with a benzimidazole and a water-miscible solvent, thereby forming said composition.

9. The process according to claim 8 wherein said benzimidazole is triclabendazole.

10. The composition according to claim 1 wherein the one or more surfactants are present in a total amount between 40% w/v and 60% w/v.

11. The composition according to claim 1 wherein one of the one or more surfactants is Polysorbate 80 which is present in an amount between 30% w/v and 60% w/v.

12. The composition according to claim 11, wherein Polysorbate 80 is present in an amount between 40% w/v and 60% w/v.

13. The composition according to claim 1 wherein one of the one or more surfactants is PEG-35 Castor Oil.

14. The composition according to claim 13, further comprising sorbitan monooleate.

15. The composition according to claim 1, wherein one of the one or more surfactants is PEG-400.

16. The composition according to claim 15, further comprising sucrose monolaurate.

17. The oral veterinary composition of claim 1 which comprises Polysorbate 80, a water-miscible solvent, propylene glycol dicaprylate/dicaprate, a benzimidazole anthelmintic compound and moxidectin, wherein the composition is non-aqueous.

18. The composition according to claim 17, further comprising sorbitan monooleate.

* * * * *